US006452007B1

(12) United States Patent
Havens et al.

(10) Patent No.: US 6,452,007 B1
(45) Date of Patent: Sep. 17, 2002

(54) CRYSTAL FORMS OF 1-[5-METHANESULFONAMIDOINDOLYL-2-CARBONYL]-4-[3-(1-METHYLETHYLAMINO)-2-PYRIDINYL] PIPERAZINE

(75) Inventors: Jeffrey L. Havens, Mattawan; Donald P. Smith, Kalamazoo; Michael S. Bergren, Portage; Mark A. Lyster, Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 08/732,254

(22) PCT Filed: Mar. 1, 1995

(86) PCT No.: PCT/US95/02166

§ 371 (c)(1),
(2), (4) Date: Sep. 30, 1996

(87) PCT Pub. No.: WO95/28398

PCT Pub. Date: Oct. 26, 1995

Related U.S. Application Data

(63) Continuation of application No. 08/311,780, filed on Sep. 23, 1994, now abandoned, which is a continuation-in-part of application No. 08/227,860, filed on Apr. 15, 1994, now abandoned.

(51) Int. Cl.[7] .......................................... C07D 401/12
(52) U.S. Cl. ................................ 544/364; 514/253.09
(58) Field of Search ......................................... 544/364

(56) References Cited

U.S. PATENT DOCUMENTS

| 3,565,924 | A |   | 2/1971  | DeLuca et al. ........... 260/397.2 |
| 3,833,622 | A |   | 9/1974  | Babcock et al. .......... 260/397.2 |
| 4,504,657 | A |   | 3/1985  | Bouzard et al. ............... 544/30 |
| 4,521,431 | A |   | 6/1985  | Crookes ...................... 514/471 |
| 5,489,593 | A | * | 2/1996  | Palmer et al. ............... 514/252 |
| 5,563,142 | A | * | 10/1996 | Palmer et al. ............... 514/253 |
| 5,599,930 | A | * | 2/1997  | Romero et al. .............. 544/121 |

FOREIGN PATENT DOCUMENTS

WO           91/09849     *   7/1991

OTHER PUBLICATIONS

Romero et al, *J. Med. Chem. 36* p 1505, May 14, 1993.*
Dueweke et al, Antimicrob. Agents Chemother. 37, p 1127, May 1993.*
Byrn, S. R., Solid–State Chemistry of Drugs, New York, Academic Press (1982).
Kuhnert–Brandstatter, M., Thermomiscroscopy In The Analysis of Pharmaceuticals, New York, Pergamon Press (1971).
Haleblian et al. J. Pharm. Sci. 58, 911 (1969).

* cited by examiner

*Primary Examiner*—Emily Bernhardt
(74) *Attorney, Agent, or Firm*—Bruce Stein

(57) ABSTRACT

The present invention relates to two novel crystal forms of a known compound, 1-[5-Methanesulfonamidoindolyl-2-carbonyl]-4-[3-(1-methylethylamino)-2-pyridinyl] piperazine monomethanesulfonate salt, which are useful for treating humans who are HIV positive, which are identified by a powder X-ray diffraction spectrum known commonly as the "S" and "T" forms.

2 Claims, No Drawings

CRYSTAL FORMS OF 1-[5-METHANESULFONAMIDOINDOLYL-2-CARBONYL]-4-[3-(1-METHYLETHYLAMINO)-2-PYRIDINYL] PIPERAZINE

This application is the continuation (national phase) of International Application No. PCT/US95/02166, International Filing Date Mar. 1, 1995, which was a continuation of U.S. patent application Ser. No. 08/311,780, filed Sep. 23, 1994, abandoned which was a continuation-in-part of U.S. patent application Ser. No. 08/227,860, filed Apr. 15, 1994, abandoned.

BACKGROUND OF THE INVENTION

1. Field of the Invention

The field of the invention is crystal forms of a known compound, 1-[5-methanesulfonamidoindolyl-2-carbonyl]-4-[3-(1-methylethyl-amino)-2-pyridinyl]piperazine monomethanesulfonate salt, which is a pharmaceutical useful in treating individuals who are HIV positive.

2. Description of the Related Art

It is known to those skilled in the art that solids including pharmaceuticals often have more than one crystal form and this is known as polymorphism. Numerous examples are cited in the standard references of solid state properties of pharmaceuticals, Byrn, S. R., Solid-State Chemistry of Drugs, New Your, Academ. Press (1982); Kuhnert-Brandstatter, M., Thermomiscroscopy In The Analysis of Pharmaceuticals, New York, Pergamon Press (1971) and *J. Pharm. Sci.*, 58, 911 (1969). Byrn states that, in general, polymorphs exhibit different physical characteristics including solubility and physical and chemical stability. It is important to note that there is no reliable method to predict the observable crystal structures of a given drug or to predict the existence of polymorphs with desirable physical properties.

U.S. Pat. No. 3,565,924 discloses and claims 25-hydroxycocalciferol (25-HCC) which is a solid. Even in view of this prior art the United States Patent Office allowed U.S. Pat. No. 3,833,622 to a novel crystal form 25-HCC hemihydrate.

U.S. Pat. No. 4,521,431 discloses forms 1 and 2 of ranitidine hydrochloride.

U.S. Pat. No. 4,504,657 claims "crystalline 7-[D-α-(p-hydroxyphenyl)acetamido]-3-methyl-3-cephem-4-carboxylic acid monohydrate.

International Publication No. WO 91/09849 (EXAMPLE 105) discloses 1-[5-methanesulfonamidoindolyl-2-carbonyl]4-[3-(1-methylethylamino)-2-pyridinyl] piperazine. *Antimicrobial Agents & Chemotherapy*, 1127–31 (May 1993) discloses 1-[5-methanesulfonamidoindolyl-2-carbonyl]-4-[3-(1-methylethylamino)-2-pyridinyl] piperazine free base. The *Journal of Medicinal Chemistry*, 36, 1505 (1993) discloses 1-[5-methanesulfonamidoindolyl-2-carbonyl]-4-[3-(1-methylethylamino)-2-pyridinyl] piperazine monomethanesulfonate salt in the "S" crystal form.

SUMMARY OF INVENTION

Disclosed is 1-[5-methanesulfonamidoindolyl-2-carbonyl]-4-[3-(1-methylethylamino)-2-pyridinyl] piperazine monomethanesulfonate salt known as the "S" form with a powder X-ray diffraction spectrum of that set forth in the claims.

Also disclosed is 1-[5-methanesulfonamidoindolyl-2-carbonyl]-4-[3-(1-methylethylamino)-2-pyridinyl] piperazine monomethanesulfonate salt known as the "T" form with a powder X-ray diffraction spectrum of that set forth in the claims.

DETAILED DESCRIPTION OF THE INVENTION

1-[5-Methanesulfonamidoindolyl-2-carbonyl]-4-[3-(1-methylethylamino)-2-pyridinyl)-piperazine is known, see International Publication No. WO 91/09849 (EXAMPLE 105). 1-[5-Methanesulfonamidoindolyl-2-carbonyl]-4-[3-(1-methylethylamino)-2-pyridinyl]piperazine monomethanesulfonate salt is also known, see *Journal of Medicinal Chemistry*, 36, 1505 (1993) and *Antimicrobial Agents & Chemotherapy*, 1127–31 (May 1993).

The "S" crystal form (also known as form VIII) of 1-[5-methanesulfonamidoindolyl-2-carbonyl]4-[3-(1-methylethylamino)-2-pyridinyl]piperazine monomethanesulfonate salt is produced by starting with 1-[5-methanesulfonamidoindolyl-2-carbonyl]-4-[3-(1-methylethylamino)-2-pyridinyl]piperazine monomethanesulfonate salt in other than the "S" form and dissolving it in a dissolving solvent selected from the group consisting of methanol, ethanol, acetonitrile, dimethyl sulfoxide and dimethylformamide or mixture thereof; it is preferred that the dissolving solvent is methanol. When starting with the free amine, methylene chloride can be used as a co-dissolving solvent preferably with methanol, but alone will not appreciably dissolve the starting material. To the solution of the salt in the dissolving solvent is added a sufficient quantity of crystallizing solvent, or mixtures thereof, which is selected from the group consisting of acetone, acetonitrile, isopropanol, n-propanol, methyl t-butyl ether, toluene, ethyl acetate, n-propyl acetate, i-propyl acetate, tetrahydrofuran, toluene or any isomer of xylene, hexane or heptane; it is preferred that the crystallizing solvent be acetone. It is preferred to add a very small amount of the desired crystal form as it hastens crystallization of the desired "S" form. After the 1-[5-methanesulfonamidoindolyl-2-carbonyl]-4-[3-(1-methylethylamino)-2-pyridinyl]piperazine monomethanesulfonate salt crystallizes, it is filtered and dried as is known to those skilled in the art.

When the "S" crystal form of 1-[5-methanesulfonamidoindolyl-2-carbon-yl]-4-[3-(1-methylethylamino)-2-pyridinyl]piperazine monomethanesulfonate salt is desired, it is preferred to dissolve the 1-[5-methanesulfonamidoindolyl-2-carbon-yl]-4-[3-(1-methylethylamino)-2-pyridinyl]piperazine monomethanesulfonate salt in methanol to give a concentration of about 1 g of compound/5 ml of methanol. This mixture is then concentrated atmospherically to a concentration of about one molar by reflux. While maintaining reflux, acetone (about 4 ml/g of 1-[5-methanesulfonamidoindolyl-2-carbonyl]4-[3-(1-methylethylamino)-2-pyridinyl]piperazine monomethanesulfonate salt) is added over a short period, for example five or ten minutes. At this point it is desirable and preferred to seed the crystallization with a small amount of the "S" crystal form. The mixture is stirred at reflux until crystallization occurs. The mixture can be filtered while hot or cooled.

An alternative procedure is to start with 1-[5-methanesulfonamidoindolyl-2-carbonyl]4-[3-(1-methylethylamino)-2-pyridinyl]piperazine free base and produce the methanesulfonic acid salt at the same time as the crystallization, see EXAMPLEs 2 and 8, which is the preferred method of practicing the invention on large scale. For small scale (laboratory or bench size) and infrequent runs the processes of EXAMPLEs 1, 4 and 6 are preferred.

When it is desired to start with the free base and acetonitrile as the dissolving solvent, at temperatures below 400 a solvated crystal form is produced. On drying, the acetonitrile is removed from the solid product and a desolvated crystal form results. When starting with the free base and methanol as the dissolving solvent and using isopropanol as the crystallizing solvent, none of the undesired crystal form that occurs with acetonitrile and low temperature occurs, but the crystals can agglomerate which can make drying more difficult. When acetone is used as the crystallizing solvent, the agglomeration problem does not occur.

The "T" crystal form (also known as form XI) of 1-[5-methanesulfonamidoindolyl-2-carbonyl]4-[3-(1-methylethylamino)-2-pyridinyl]piperazine monomethanesulfonate salt is produced by starting with 1-[5-methanesulfonamidoindolyl-2-carbonyl]-4-[3-(1-methylethylamino)-2-pyridinyl]piperazine monomethanesulfonate salt in other than the "T" form and recrystallizing from a dissolving solvent (as identified above). The use of a crystallizing solvent (identified above) is optional. The "T" form of 1-(5-methanesulfonamidoindolyl-2-carbonyl]-4-[3-(1-methylethylamino)-2-pyridinyl]piperazine monomethanesulfonate salt can be produced from either the free base or a different crystal form of the mesylate salt as is described above for the "S" crystal form. For obtaining the "T" form it is preferred to have a concentration of about 1 g of compound/ml of dissolving solvent, especially when the dissolving solvent is methanol. When producing the "T" crystal form, it is preferred to seed the reaction mixture with previously obtained "T" crystal.

Both "S" and "T" forms of 1-[5-methanesulfonamidoindolyl-2-carbonyl]-4-[3-(1-methylethylamino)-2-pyridinyl]piperazine monomethanesulfonate salt are used in the same way as described for 1-[5-methanesulfonamidoindolyl-2-carbonyl]-4-[3-(1-methylethylamino)-2-pyridinyl]piperazine in International Publication No. WO 91/09849. More specifically, the "S" and "T" forms of 1-[5-methanesulfonamidoindolyl-2-carbonyl]-4-[3-(1-methylethylamino)-2-pyridinyl] piperazine monomethanesulfonate salt are useful in the treatment of AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than 200/m$^3$ in the peripheral blood. The "S" and "T" forms of 1-[5-methanesulfonamidoindolyl-2-carbonyl]-4-[3-(1-methylethylamino)-2-pyridinyl]piperazine monomethanesulfonate salt can be given orally. Suitable dosage forms include tablets, capsules, suspensions, solutions and elixirs.

An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on whether "S" or the "T" form of 1-[5-methanesulfonamidoindolyl-2-carbonyl]-4-[3-(1-methylethylamino)-2-pyridinyl]piperazine monomethanesulfonate salt is used, the particular condition being treated, the severity of the condition being treated, the age, weight, general physical condition of the particular patient, other medication the individual may be taking as is well known to those skilled in the art and can be more accurately determined by measuring the blood level or concentration of the 1-[5-methanesulfonamidoindolyl-2-carbonyl]-4-[3-(1-methylethylamino)-2-pyridinyl]piperazine monomethanesulfonate salt in the patient's blood and/or the patient's response to the particular condition being treated.

Patients who are HIV positive but asymptomatic would typically be treated with lower oral doses (about 0.2 to about 100 mg/kg/day. ARC (AIDS-related complex) and AIDS patients would typically be treated with higher oral doses (about 1 to about 500 mg/kg/day).

The "S" and "T" forms of 1-[5-methanesulfonamidoindolyl-2-carbonyl]-4-[3-(1-methylethylamino)-2-pyridinyl]piperazine monomethanesulfonate salt of this invention can be be used in conjunction with other antiviral agents such as AZT.

The exact dosage and frequency of administration depends on the particular condition being treated, the severity of the condition being treated, the age, weight, general physical condition of the particular patient, other medication the individual may be taking as is well known to those skilled in the art and can be more accurately determined by measuring the blood level or concentration of CD4 in the patient's blood and/or the patient's clinical response.

DEFINITIONS

The definitions and explanations below are for the terms as used throughout this entire document including both the specification and the claims.

All temperatures are in degrees Centigrade.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

"S" Crystal Form Of 1-[5-methanesulfonamidoindolyl-2-carbon-yl]-4-[3-(1-methylethylamino)-2-pyridinyl]piperazine Monomethanesulfonate Salt From A Different Crystal Form 1-[5-Methanesulfonamidoindolyl-2-carbonyl]-4-[3-(1-methylethylamino)-2-pyridinyl]-piperazine monomethanesulfonate salt (crystal form XI, 25 g) is dissolved in methanol (125 ml) by refluxing. The mixture is concentrated atmospherically to a volume of 40–45 ml. While maintaining reflux, warm acetone (100 ml) is added over 5 min. The mixture is held at reflux and crystals are observed within 30 min. The slurry is stirred at reflux for a total of 60 min and then filtered. The filter cake is washed with acetone (100 ml) and dried to give the title compound, mp 228–232°.

Example 2

"S" Crystal Form Of 1-[5-methanesulfonamidoindolyl-2-carbon-yl]-4-[3-(1-methylethylamino)-2-pyridinyl]piperazine Monomethanesulfonate Salt From The Free Base 1-[5-Methanesulfonamidoindolyl-2-carbonyl]-4-[3-(1-methylethylamino)-2-pyridinyl]-piperazine (THF solvate, 100 g, 0.18 moles) is slurried in methanol to which is added methanesulfonic acid (19.6 g, 0.20 moles). The mixture is warmed to 40° and isopropanol (325 ml) is added. The mixture is held at 37–42° and crystals are observed within 2–3 hours. The slurry is cooled over 2 hr to 150 and filtered. The cake is washed with isopropanol (100 ml) and methyl-t-butyl ether (250 ml) then dried to give the title compound, mp 221–228°.

Example 3

"S" Crystal Form Of 1-[5-methanesulfonamidoindolyl-2-carbon-yl]-4-[3-(1-methylethylamino)-2-pyridinyl]piperazine Monomethanesulfonate Ssalt From The Free Base 1-[5-Methanesulfonamidoindolyl-2-carbonyl]-4-[3-(1-methylethylamino)-2-pyridinyl]-piperazine (THF solvate, 6.58 kg, 12.77 moles) in methanol (50 l) and methylene chloride (150 l) is filtered through a 0.6 micron filter, then rinsed with methylene chloride (50 l). The mixture is concentrated under reduced pressure at 10° to 10 l, diluted with acetonitrile (160 kg) and concentrated to 10 l. The residue is then slurried in acetonitrile (240 l), the mixture is heated to 63° and methanesulfonic acid (1.29 kg, 13.4 moles) is added. The mixture is heated further to 70–75° and after stirring at that temperature for 4.5 hr it is cooled to 32°. The product is collected on a filter, rinsed with acetonitrile (50 l) and dried to give the title compound, mp 222–229°.

Example 4

"T" Crystal Form Of 1-[5-methanesulfonamidoindolyl-2-carbon-yl]-4-[3-(1-methylethylamino)-2-pyridinyl]piperazine Monomethanesulfonate Salt From Crystal Form VIII 1-[5-Methanesulfonamidoindolyl-2-carbonyl]-4-[3-(1-methylethylamino)-2-pyridinyl]- piperazine monomethanesulfonate salt (crystal form VIII, 25.0 g, 0.045 moles) is dissolved in methanol (25 ml) at reflux. After an hour at reflux crystals are observed. The slurry is filtered without cooling and dried to give the title compound, mp 213–233°.

Example 5

"T" Crystal Form Of 1-[5-methanesulfonamidoindolyl-2-carbon-yl]-4-[3-(1-methylethylamino)-2-pyridinyl]piperazine Monomethanesulfonate Salt From The Free Base 1-[5-Methanesulfonamidoindolyl-2-carbonyl]-4-[3-(1-methylethylamino)-2-pyridinyl]- piperazine (THF solvate, 100.0 g, 0.18 moles) is slurried in methanol (250 ml) to which is added methanesulfonic acid (19.0 g, 0.21 moles). The mixture is heated at reflux until dissolved and then concentrated atmospherically to 150 ml volume. The mixture is seeded with 10 mg of previously isolated "T" crystal form and reflux is continued until crystallization is observed. The slurry is held at reflux for 16 hr and filtered without cooling and dried to give the title compound.

Example 6

"T" Crystal Form Of 1-[5-methanesulfonamidoindolyl-2-carbon-yl]-4-[3-(1-methylethylamino)-2-pyridinyl]piperazine Monomethanesulfonate Salt From Crystal Form VIII 1-[5-Methanesulfonamidoindolyl-2-carbonyl]-4-[3-(1-methylethylamino)-2-pyridinyl]- piperazine monomethanesulfonate salt (crystal form VIII, 104.9 g, 0.19 moles) is dissolved in methanol (150 ml) by refluxing. The solution is concentrated atmospherically to a 175 ml volume. While maintaining reflux, warn acetone (100 ml) is added over 15 minutes. Crystals are observed within 30 minutes at which time additional acetone (175 ml) is added over 70 minutes. The slurry is stirred at reflux for a total of 2 hr, cooled to 15°, and then filtered. The filter cake is washed with acetone (200 ml) and dried to give the title compound, mp 212–228°.

Example 7

"T" Crystal Form Of 1-[5-methanesulfonamidoindolyl-2-carbon-yl]-4-[3-(1-methylethylamino)-2-pyridinyl]piperazine Monomethanesulfonate Salt From Crystal Form VIII 1-[5-Methanesulfonamidoindolyl-2-carbonyl]4-[3-(1-methylethylamino)-2-pyridinyl]- piperazine monomethanesulfonate salt (crystal form VIII, 25.0 g, 0.045 moles) is slurried at reflux in a mixture of methanol/acetone (1/1, 50 ml). The slurry is seeded with 10 mg of previously isolated "T" crystal form. After refluxing for 2–3 hr the slurry is cooled to 15°, filtered, washed with acetone (50 ml and dried to give the title compound, mp 213–2280.

Example 8

"T" Crystal Form Of 1-[5-methanesulfonamidoindolyl-2-carbon-yl]4-[3-(1-methylethylamino)-2-pyridinyl]piperazine Monomethanesulfonate Salt 1-[5-methanesulfonamidoindolyl-2-carbonyl]-4-[3-(1-methylethylamino)-2-pyridinyl]piperazine (free base, THF solvate, 100.0 g, 0.18 moles) is slurried in methanol (250 ml) to which is added methanesulfonic acid (17.65 g, 0.18 moles). The mixture is heated at reflux until dissolved and then concentrated atmospherically to about 300 ml volume at which time it is seeded with 10–15 mg of previously isolated 1-[5-methanesulfonamidoindolyl-2-carbonyl]-4-[3-(1-methylethylamino)-2-pyridinyl]piperazine monomethanesulfonate salt "T" crystal form. The atmospheric concentration is continue to a 200 ml volume. While maintaining reflux, acetone (175 ml) is added over about 10 minutes. The mixture is seeded again with 10–15 mg of previously isolated 1-[5-methanesulfonamidoindolyl-2-carbon-yl]-4-[3-(1-methylethylamino)-2-pyridinyl]piperazine monomethanesulfonate salt "T" crystal form and held at reflux. Crystals are observed within 30 minutes and the slurry is maintained at reflux for an an additional 30 minutes. At that time the atmospheric distillation is restarted and acetone is added so as to maintain a constant volume. When 250 ml of acetone had been added the distillation is ended and the mixture cooled to 150. After stirring the slurry for about two hours it is filtered and the filter cake is washed with acetone. The product is dried to give 88.96 g of the title compound, mp 214–227°.

CHART A

1-[5-Methanesulfonamidoindolyl-2-carbonyl]-4-[3-(1-methylethylamino)-2-pyridinyl]piperazine has the following chemical structural formula

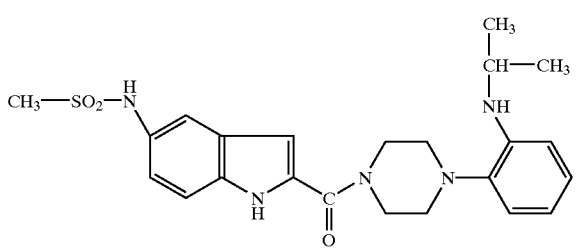

What is claimed is:

1. 1-[5-Methanesulfonamidoindolyl-2-carbonyl]-4-[3-(1-methylethylamino)-2-pyridinyl]-piperazine monomethanesulfonate salt known as the "S" form with a powder X-ray diffraction spectrum of:

| Two-Theta Angle (°) | d-spacing (Å) | Relative Instensity (%) |
|---|---|---|
| 27.10 | 3.288 | 20.1 |
| 24.55 | 3.623 | 28.0 |
| 23.40 | 3.799 | 28.6 |
| 23.10 | 3.847 | 36.8 |
| 22.25 | 3.992 | 100.0 |
| 21.55 | 4.120 | 64.9 |
| 20.75 | 4.277 | 34.3 |
| 19.30 | 4.595 | 69.1 |
| 18.25 | 4.857 | 28.9 |
| 17.40 | 5.093 | 15.4 |
| 17.10 | 5.181 | 52.5 |
| 14.55 | 6.083 | 22.4 |
| 13.55 | 6.530 | 30.3 |
| 13.05 | 6.779 | 14.8 |
| 6.40 | 13.799 | 56.2 | where Two-Theta Angle is measured in degrees, d-Spacing is measured in angstroms and where Relative Intensity is the intensity percentage of each peak relative to the strongest peak at 22.25 degree.

2. 1-[5-Methanesulfonamidoindolyl-2-carbonyl]-4-[3-(1-methylethylamino)-2-pyridinyl]-piperazine monomethanesulfonate salt known as the "T" form with a powder X-ray diffraction spectrum of:

| Two-Theta Angle (°) | d-spacing (Å) | Relative Instensity (%) |
|---|---|---|
| 28.80 | 3.097 | 19.9 |
| 27.90 | 3.195 | 18.5 |
| 27.10 | 3.288 | 28.3 |
| 25.00 | 3.559 | 21.5 |
| 25.00 | 3.559 | 21.5 |
| 23.10 | 3.847 | 64.6 |
| 22.75 | 3.906 | 22.6 |
| 21.95 | 4.046 | 39.6 |
| 20.40 | 4.350 | 82.7 |
| 18.75 | 4.729 | 60.2 |
| 18.40 | 4.818 | 100.0 |
| 13.35 | 6.627 | 46.4 |
| 12.35 | 7.161 | 26.6 |
| 9.70 | 9.111 | 23.8 |
| 6.65 | 13.281 | 56.5 | where Two-Theta Angle is measured in degrees, d-Spacing is measured in angstroms and where Relative Intensity is the intensity percentage of each peak relative to the strongest peak at 18.40 degree.

* * * * *